(12) United States Patent
Cohen et al.

(10) Patent No.: US 6,454,806 B1
(45) Date of Patent: Sep. 24, 2002

(54) SPINAL SURGICAL PROSTHESIS

(75) Inventors: Howard Cohen, New York County; Ladislau Biro, Middlesex County; Matthew S. Cohen, New York County, all of NY (US)

(73) Assignee: Advanced Prosthetic Technologies, Inc., Metuchen, NJ (US)

( * ) Notice: Subject to any disclaimer, the term of this patent is extended or adjusted under 35 U.S.C. 154(b) by 0 days.

(21) Appl. No.: 09/360,796

(22) Filed: Jul. 26, 1999

(51) Int. Cl.[7] .................................................. A61F 2/44
(52) U.S. Cl. .................................................... 623/17.15
(58) Field of Search ........................... 623/17.13, 17.15, 623/17.16

(56) References Cited

U.S. PATENT DOCUMENTS

| | | | | |
|---|---|---|---|---|
| 4,309,777 A | * | 1/1982 | Patil | 623/17.15 |
| 5,865,848 A | * | 2/1999 | Baker | 623/17 |
| 5,928,284 A | * | 7/1999 | Mehdizadeh | 623/17.15 |
| 6,176,881 B1 | * | 1/2001 | Schar et al. | 623/17.15 |
| 6,193,756 B1 | * | 2/2001 | Studer et al. | 623/17.15 |
| 6,200,348 B1 | * | 3/2001 | Biedermann et al. | 623/17.16 |

* cited by examiner

*Primary Examiner*—Bruce Snow
(74) *Attorney, Agent, or Firm*—Howard C. Miskin; Gloria Tsui-Yip

(57) ABSTRACT

A prosthesis in the form of a cage having opposed complimentary bearing surface assemblies. The bearing surface assemblies moveable towards and away from each other. The moving mechanism being part of the bearing surface assemblies. Each of the bearing surface assemblies having an outer bearing surface whereby movement of one bearing surface assembly in one direction will move the bearing surface assemblies away from each other and movement in the opposite direction will move the bearing surface assemblies towards each other.

18 Claims, 15 Drawing Sheets

SPINAL SURGICAL PROSTHESIS

FIELD OF INVENTION

The present invention relates to an improved spinal surgical prosthesis and more particularly to apparatus and methods for achieving stability of adjacent vertebrae and preserving the inter-disc space following disectomy by internal fixation or fusion.

BACKGROUND OF THE INVENTION

Fusion commonly performed for adjacent bone structures and those not adjacent provides for long term replacement as a result of degenerative or deteriorated disorders in bone.

An inter-vertebral disc is a ligamentous cushion disposed between vertebrae and as a result of injury, disease or other disorders may deteriorate in part or in whole, thereby leading to mechanical instability and painful disc translocations and often necessitating bed rest or hospitalization. If left untreated possible subsequent involvement of adjacent nerves and muscular involvement may occur. In such cases, if treatment is delayed, permanent damage to the nerves may result in muscular atrophy and severe dysfunction.

Procedures for disc surgery may involve partial or total excision of the injured disc portion and replacement with biocompatible devices of bone or bone-like material.

EARLY TECHNIQUES

Bone material was simply disposed between the adjacent vertebrae, typically at the posterior aspect of the vertebrae and the spinal column was stabilized by way of a plate or rod connecting the involved vertebrae. However, the use of bone may require undesired additional surgery and is of limited availability in its most useful form. In addition, the risk of infection and rejection is a significant consequence. In any event, bone is only marginally structural and with bone it is difficult to stabilize both the implant against dislodgment and stabilize the adjacent vertebrae. It becomes desirable to find solutions for stabilization of an excised disc space by fusing the vertebrae between their respective end plates without the need for anterior or posterior plating or rods.

PRIOR ART

A review of the prior art clearly reveals attempts to achieve such solutions in two distinct areas, namely:

I. Static inter-body fusion devices

II. Adjustable inter-body fusion devices that can restore and stabilize varying heights of the intra-discal space.

I. Static Inter-Body Fusion Devices

An extensive number of static inter-body fusion devices commonly called "cages" have evolved for replacement of a damaged disc while still maintaining stability of the disc inter-space between the adjacent vertebrae.

However, existing static inter-body fusion devices encountered some problems. They require drilling, boring or tapping of the end plates which sometimes results in removal of an excessive amount of supporting bone with possible damage to adjacent structures. Moreover, threads of the implant or cage may inadvertently engage the prepared threads of the vertebrae in an improper manner so as to cause a misalignment of the vertebrae in an anterior-posterior direction as well as laterally. If a second cage is needed, it involves the drilling, boring or tapping of the vertebral end plates for both cages so that the threads direct the cages into their proper respective positions. Such preparation requires highly skilled precision that may not be afforded or attainable under normal working conditions.

When a second cage is inserted, due to the unevenness of the vertebral end plates concave engaging surfaces, an unwanted increase in the inter-vertebral space may result in the loosening and possible dislodgment of the initially placed implant cage.

The anatomical configurations of the vertebrae necessitates that the two cages be positioned at an angle in respect to each other so as to be totally within the confines of the lateral borders of the vertebrae involved.

Use of tapered cages that are dimensionally greater in height anteriorally than posteriorally so as to provide the proper lordosis when such cage implants are employed creates complications. When the posterior approach is utilized and drilling, boring or tapping is necessary for placing threads on the vertebral end plates, difficulties exist in creating threads that will have a pitch compatible with those exhibited by the threads of such cages. A further complication is present when utilizing tapered cages via the posterior approach in that the dimensionally higher anterior threaded portion of the tapered cage is initially inserted and advanced to its most anterior final resting position. These cages are self-tapping to some degree and may result in the unwanted excessive removal of bone from the posterior portion of the lumbar segments where the lordosis is greatest.

Drilling and other types of preparation of the vertebral end plates may result in the removal of excessive amounts of supporting bone, and may cause the cage implants to rest upon the cancellous portion of the vertebrae. In such instances the cages may settle into said vertebrae resulting in a decreased inter-vertebral space other than that desired with subsequent complications of stabilization, pain and discomfort.

II. Adjustable Inter-Body Fusion Devices

These are designed for restoring and maintaining the inter-vertebral space thereby providing for the normal contour of the fused spinal segments. Once the disc is removed, the normal lordotic or kyphotic curvature is eliminated and adjustable inter-body fusion implants are employed for re-establishing the proper curvature and stabilization of the spine.

Adjustable inter-body fusion devices have universal applicability and may eliminate the need for surgical preparation of the vertebral end plates such as contouring of bone and drilling, boring and tapping of said vertebral end plates. Such devices restore and preserve the inter-space and the integrity of the adjacent vertebrae thereby making the selection of the proper implant easier. They result in preservation of the highly specialized weight bearing cortical bone thereby preventing end plate perforation into the highly vascular cancellous bone marrow and unwanted subsequent bleeding may result in many complications due to excessive blood loss risks (e.g. hypoglycemic shock, transfusion, and possible diseases such as hepatitis and Acquired Immune Deficiency Syndrome, etc.),. Another advantage of such devices is the elimination of incorrect implant size selection as no significant amount of bone is removed and the correct size implants are easily fitted to restore the proper inter-space. In addition, the implant is self-stabilizing without the use of threads and may be further enhanced by surface treating of the implant for bone in-growth and osseous integration of the implant.

DESCRIPTION OF THE RELATED ART

The following patents disclose Static Inter-Body Fusion Devices: U.S. Pat. Nos. 5,785,710; 5,782,919; 5,766,253; 5,609,636; 5,425,772; 4,878,915; 4,501,269; 4,961,240 and 5,055,104.

The following patents disclose Adjustable Inter-Body Fusion devices: U.S. Pat. Nos. 5,782,832; 5,766,199; 5,702,455; 5,609,635; 5,336,223; 5,306,310.

ADVANTAGES OF INVENTION

The present invention overcomes the disadvantages represented by the prior art by not requiring drilling procedures for threaded engagement of adjacent vertebrae and subsequent end plate preservation. It restores and preserves the disc inter-vertebral space with the proper curvature of the spine. As taught by this invention, the methods and devices for insertion following disc removal requires no specialized surgical technique and allows for precise placement of the device and subsequent re-establishment of the proper inter-vertebral space and lordosis by either an anterior or posterior surgical approach. Further, this invention permits precise implant size to fit within the space allowed and not endanger or damage adjacent structures. Hence, incorrect implant size selection and the need for a variety of implant sizes is eliminated. An added advantage is, if removal is necessary it would not result in iatrogenic destruction of the adjacent vertebrae. Also, spinal stability is obtained without the use of threads since such threads may adversely affect the vertebrae themselves.

SUMMARY OF INVENTION

The present invention is an inter-space implant utilized to replace a damaged disc. The present invention is clearly an improvement over the prior art providing an implant prosthesis intrinsically participating in this fusion process, self-stabilizing to the spinal segments, consistent with conventional methods of disectomy and uniquely and novel consistent with the preservation of the integrity of the adjacent vertebrae.

The present invention comprises an artificial implant for the purpose of which is to aid in and directly cause bone fusion across an inter-vertebral space following the removal of a damaged disc. Said prostheses are biocompatible, structurally load bearing devices, stronger than bone, capable of withstanding the forces generated within the spinal inter-space. They have a plurality of openings of specific size which can be filled with fusion promoting material by inducing bone growth and osseous integration with the adjacent vertebrae forming a bony bond to the implants and each other. The implant bone-contacting surface may be textured, designed or otherwise treated by any known technologies to achieve bone in-growth and fusion to the implants to enhance stability of the implant and to expedite the fusion. The improved devices are configured and designed so as to promote their own stability within the vertebral inter-space to resist dislodgment and stabilize the adjacent vertebrae.

The present implant is made of a biocompatible material and has means if desired for increasing osseous integration, controlling hemostasis and preventing infection. It establishes proper spinal curvature or lordosis and kyphosis and capable of reducing a vertebral listness (a forward or backward translation of one vertebrae upon another as well as lateral misalignment of said vertebrae). It gives increased safety and precision which provides complete and easy visualization of the structures involved and adjacent vital structures (e.g. organs, neural structures and blood vessels and related bony surfaces). It also eliminates the need for a second surgical procedure to harvest bone. It also provides the method and material that is resorbable for additional means of stabilization to be used in conjunction with the implant prosthesis for certain conditions that require additional stabilization for osseous integration. It may be used in distraction osteogenesis procedures in order to increase bone length and/or for inducing bone growth and osseous integration of the implant, and for controlling hemostasis and pain and preventing infection during and following the surgical procedure allowing for an increased opportunity of success.

PROCEDURE FOR IMPLANT

A conventional disectomy is performed and the vertebral end plates are roughened in preparation for use of the implant prosthesis of the present invention.

In an anterior cervical device implantation a short transverse incision is made across the front of the neck and off-center, preferably to the right of the midline and directly over the diseased or otherwise disc being replaced. The platysma muscle is dissected and split and the sternocleidomastoid muscle with the carotid sheath is protected and retracted laterally. The esophagus, trachea and associated midline structures are protected and retracted medially, thus exposing the anterior aspect of the cervical spine. The disc involved is identified and removed by known, acceptable and conventional surgical methods. The adjacent vertebral end plates are gently scraped free of any remaining cartilage until diffuse fine punctuate decortication is achieved. The dimensions of the inter-space are then measured in mild distraction and compared with the stereo-tactic pre-surgical x-ray diagnostic procedures and video imaging devices which helps to determine the exact intra-discal space to be restored relative to the vertebrae involved and the undamaged disc space that exists inferiorly and superiorly to the vertebrae involved. The appropriate device or devices are selected for insertion with a specially designed device that establish the necessary space for insertion behind the anterior lips of the vertebrae. The device is activated for establishing the desired inter-vertebral space and said device is locked at the desired height. Alternatively, the prosthesis may be a single, double or multiple activated device so as to properly provide stability and the proper curvature or lordosis of the spine. Harvested bone or bone fill material commonly employed is packed into and around the implant. Alternatively a new bone fill material is provided that is a polymer capable of being polymerized into a desired shape and size via being a resorbable biocompatible photo-initiated polymer and cured via visible light. In certain situations of trauma and disease additional stabilization is required and a resorbable biocompatible photo-initiated polymer rod or plate and screws may be utilized and to be attached to the vertebrae involved as well as healthy vertebrae above and below the damaged site. Guide plates are provided for drilling holes to affix the plate and or rod to the vertebrae with the necessary screws. In extreme cases the additional stabilization may employ currently available rigid devices for such purposes. All areas are inspected and the wound is then closed in the routine manner. A further biocompatible resorbable photo-initiated polymer is provided to control hemostasis as well as controlling post-operative pain or infection. The devices may also be used in other areas of the spine, such as the thoracic and lumbar regions, utilizing both the anterior or posterior surgical approaches as selected by the surgeon.

OBJECTS OF THE INVENTION

It is the object of the present invention to provide for a means of achieving fusion of the inter-vertebral space and stabilization as a single procedure by a means consistent with the conventional method of disectomy and re-establishing the ideal and normal pre-existing disc interspace.

It is another object of the present invention to provide for a means of achieving an inter-space fusion and stabilization that is easier, quicker, safer and entails less blood loss than other known means.

It is another object of the present invention to provide for a means of achieving a one stage inter-space fusion and stabilization with minimal damage and less removal of bone from the surface of the adjacent vertebrae than other known means.

It is another object of the present invention to provide for a method and device for inter-vertebral arthrodesis and stabilization and establishing the normal and pre-exiting inter-vertebral space in an easy, quick, safe and precise manner and in addition the entire procedure is performed under direct vision and may be further guided by optical imaging computerized devices.

It is another object of the present invention to provide for a method and device of inter-vertebral arthrodesis and stabilization that allows for the inter-vertebral space to be adjusted and of variable sizes unlike any other known means and with greater simplicity and accuracy than any other known means.

It is another object of the present invention to provide for a modular prosthesis having similar and multiple attachments that allows for insertion through a small opening and then to reconstitute an inter-space occupying device much larger than would be normally inserted.

It is another object of the present invention to provide for a method and device that precisely fits the contours of any inter-space without the need to sacrifice any vertebral bone to accommodate the prosthesis and can be inserted from an anterior or posterior surgical approach if desired.

It is another object of the present invention to provide for an implant that has means for osseous integration with the adjacent vertebrae and said device having additional means to act as a shock absorber when extremely heavy forces are exerted upon said device.

It is another object of the present invention to provide for a method and device that reestablishes the normal lordosis of the spine in a simple and precise manner.

It is another object of the present invention to provide a method and biocompatible material for inducing bone growth that is easier to use than any other known materials for this purpose and can readily be shaped into a desired form and resist dislodgment. This material may also act over a prolonged period of time by being time released for this purpose.

It is another object of the present invention to provide a biocompatible material and method for use in controlling hemostasis thereby enhancing the opportunity of success for osseous integration in individuals with abnormal clotting times. The hemostatic agent may also act over a prolonged period of time to further control post- operative bleeding, especially in individuals with poor clotting times, by being time released for this purpose.

It is another object of the present invention to provide a material and method for controlling post-operative pain following the surgical procedure, and said material may be time released locally over a period of time for this purpose.

It is another object of the present invention to provide a material and method for preventing and controlling infection following the surgical procedure and said material may be time released locally and/or in combination with systemic drugs for this purpose.

It is another object of the present invention to provide a material and method for use of time released anti-tumor drugs or radiation seeds that may control or eradicate tumors related to the area of uses of said invention.

It is another object of the present invention to provide a method and device for use in distraction osteogenesis procedures unlike any other known devices and method currently employed.

These and other objects of the present invention will be apparent from review of the following documentation and accompanying drawings.

BRIEF DESCRIPTION OF THE DRAWINGS

Although the invention has been described with regard to the preferred embodiments, it is recognized that other embodiments of the present invention may be devised which would not depart from the scope of the present invention.

DESCRIPTION

In general the present invention provides two identical interlocking disc shaped parts that have an elevated, spiraling steps-like surface around the perimeter and inner walls that provide an axis and bearing surface for rotation/interlocking. When these discs are rotated toward or away from each other the discs will increase or decrease the distance between them at 10 degrees rotation by a predetermined amount. In effect, this changes the rotational motion of the discs with a linear motion.

Figure 1:
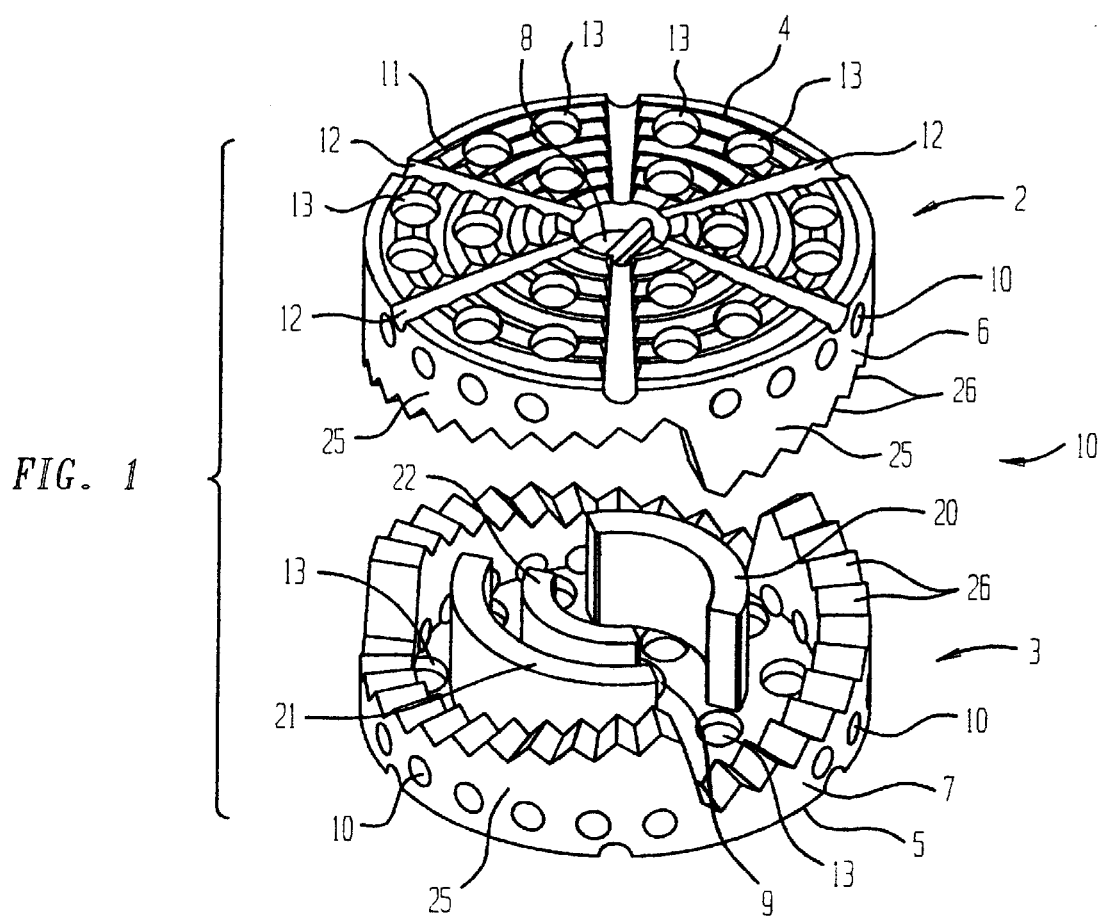
FIG. 1 is an exploded perspective view showing a prosthesis made in accordance with the present invention.
Figure 4:
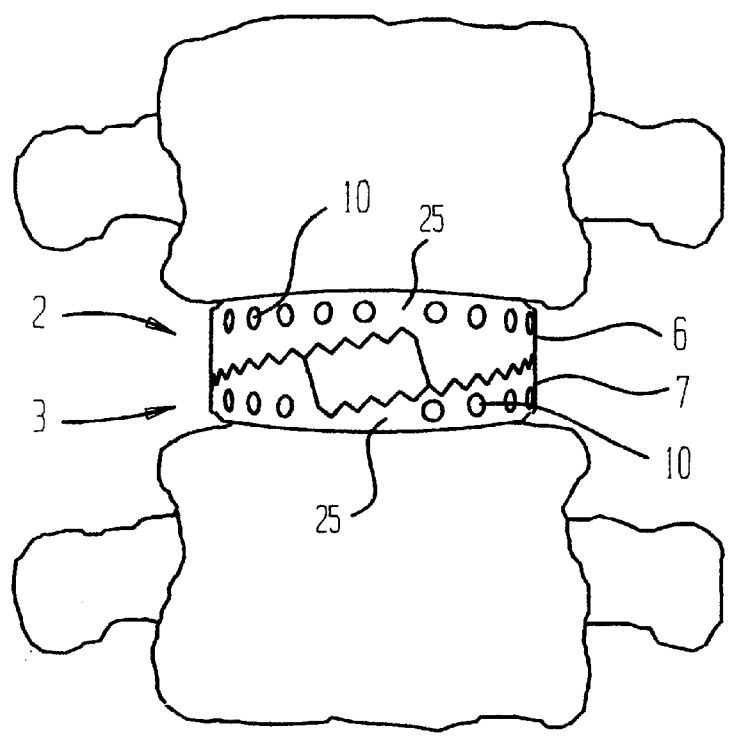
FIG. 4 is a rear view of the prosthesis as shown in FIG. 3.

Referring to the drawings, and particularly to the embodiment of the invention shown in FIGS. 1 and 4, the prosthesis or implant of the present invention comprises a cage 1 having a pair of upper and lower sections 2 and 3 which are identical to and complimentary to each other and are adapted to interfit and rotate relative to each other. The upper section 2 has a top bearing surface 4 and the lower section 3 has a bottom bearing surface 5 which is substantially identical to the top bearing surface 4. The bearing surfaces 4 and 5 are shown as being circular and have circular side-walls 6 and 7, respectively, extending at right angles from each. The top and bottom bearing surfaces 4 and 5 have a central opening 8 and 9, respectively, and the side walls 6 and 7 have a plurality of openings 10 therein. Circular ridges 11 are provided on the top and bottom bearing surfaces 4 and 5, each of which are concentrically located with respect to the central openings 8 and 9. Radiating outwardly from each central opening 8 and 9 are channels 12. A plurality of openings 13 are preferably provided in the top and bottom bearing surfaces 4 and 5. Bearing surfaces 4 and 5 are not limited to being circular in shape as shown and can be oval or having the shape of the vertebrae endplates or other shapes. Similarly, ridges 11 are not limited to being concentrically circular as shown and other shapes or non-uniformly aligned ridges may be used.

Spaced inwardly from the side walls 6 of each of the two sections 2 and 3 are a pair of opposed curved outer guide partitions 20 and 21, each of which is substantially equally spaced from the central openings 8 and 9 and equally spaced from their respective side walls 6 and 7. Each of the top and bottom sections 2 and 3 have an inner curved guide partition 22 inwardly spaced from one of the outer partitions 20 and 21. The top and bottom sections 2 and 3 are adapted to be assembled together so that the partition 21 of one section will fit between the partitions 20 and 22 of the other section, as more clearly shown in FIG. 2. This will permit the two sections 2 and 3 to rotate relative to each other while remaining in axial alignment with each other. Furthermore, the partitions 20, 21 and 22 limit the degree of rotation when partitions 20, 21 or 22 of the top section 2 is rotated until it comes in contact with the corresponding partitions 20, 22 or 21, respectively, of bottom section 3. A spring 41 is inserted in and extends between the openings 8 and 9 in order to hold the two section 2 and 3 together and biased towards each other. Other means of biasing, for example, elastic string or post can be used.

The side walls 6 and 7 of each section 2 and 3 are arranged in a plurality of inclined cam surfaces 25 which extend substantially from the bearing surfaces 4 and 5 of each and incline away from the bearing surfaces 4 and 5. In the embodiment shown in FIGS. 1 through 4, three identical cam surfaces 25 are shown on each section 2 and 3. However, it will be understood that the number of cam surfaces 25 may be increased or decreased if desired. The cam surfaces 25 of each section 2 and 3 are complimentary to each other. In the drawings, the edge of each cam surface 25 has a plurality of teeth 26. The teeth 26 and the cam surfaces 25 of each top and bottom section 2 and 3 are the same so that the teeth 26 of each will interfit with each other when the two sections 2 and 3 are assembled together. Preferably, the apexes of the teeth 26 are rounded with a radius of 0.005 inch as shown in FIG. 8B. However, different radii can be used. The sections 2 and 3 are adjusted to the desired height by rotating one section relative to the other. The cam surfaces 25 will move the sections 2 and 3 away from each other or toward each other and the teeth 26 in both sections will interfit with each other to prevent rotary displacement and to hold the sections 2 and 3 at the desired height. The openings 10 on the side walls 6 and 7 may be used to rotate one section relative to the other section by inserting a tool (not shown) therein and rotating one section relative to the other section.

Figure 3:
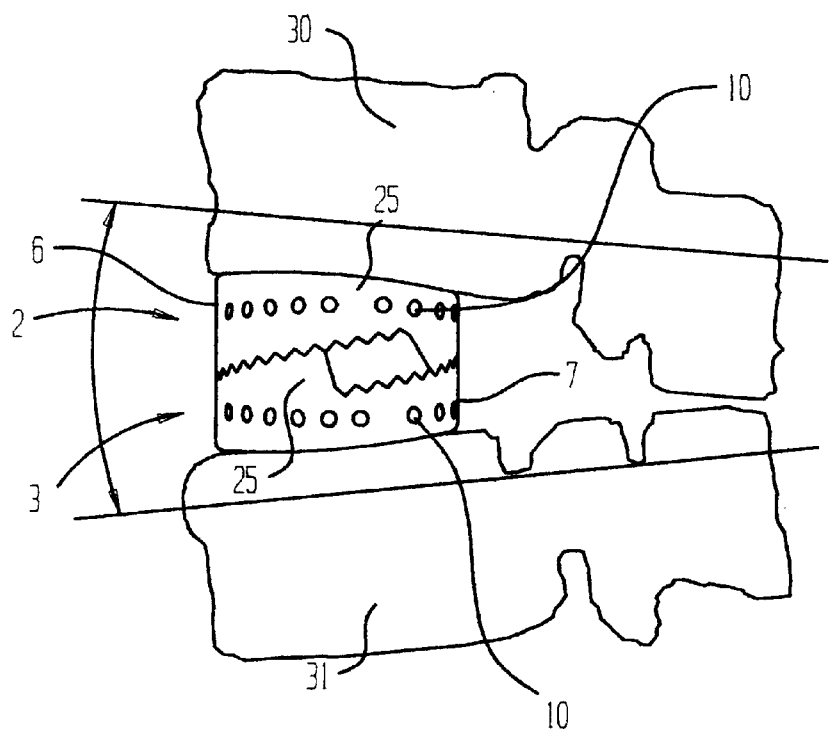
FIG. 3 is a highly simplified side view showing the prosthesis in place between vertebrae.

The two sections 2 and 3 of the cage 1 are assembled together and inserted between vertebrae 30, 31 as shown in FIGS. 3 and 4. Prior to insertion between vertebrae 30 and 31, various substance or agents 27 to promote osseous integration (e.g. De-Mineralized Bone Matrix available from Grafton Inc., which is putty-like in an uncured state for ease of placement and becomes not pliable upon curing), control post-operative bleeding, pain, infection or control or eradicate tumors may be placed between the two sections 2 and 3 and/or between cage 1 and vertebrae 30 and 31. These substance or agents 27 may be incorporated in a bio-compatible or bio-resorbable material. The bio-compatible or bio-resorbable material containing the various substance or agents 27 may be photocurable polymers, by either ultraviolet light in the range of 350–385 nanometers in wavelength or visible light in the range of 385–550 nanometers in wavelength. Furthermore, the bio-compatible or bio-resorbable material may also be colored in the uncured state and turn clear upon curing to aid in assuring visually that the polymer has been completely cured, such as photoinitiator HU-470 available from Spectra Inc.

The vertebrae 30 and 31 and the space between them have been prepared (by cleaning and otherwise) to receive the cage 1 as described hereinabove. After the cage 1 is inserted between the two vertebrae 30 and 31, the two sections 2 and 3 are rotated relative to each other until their bearing surfaces 4 and 5 make the proper contact with the opposed bearing surfaces of the vertebrae 30 and 31 in order to support the vertebrae. The ridges 11 on the bearing surfaces 4 and 5 permit the two sections to be easily rotated on the vertebrae and permit positive contact with the vertebrae. The channels 12 act as a reservoir for cartilage and other bone material to enter as the bearing surfaces 4 and 5 grasp and become enmeshed with the two sections 2 and 3 thereby fusing the cage 1 between adjacent vertebrae 30 and 31. Channels 12 may also be coated with a bone initiating or stimulating material to further promote osseous integration.

Figure 5:
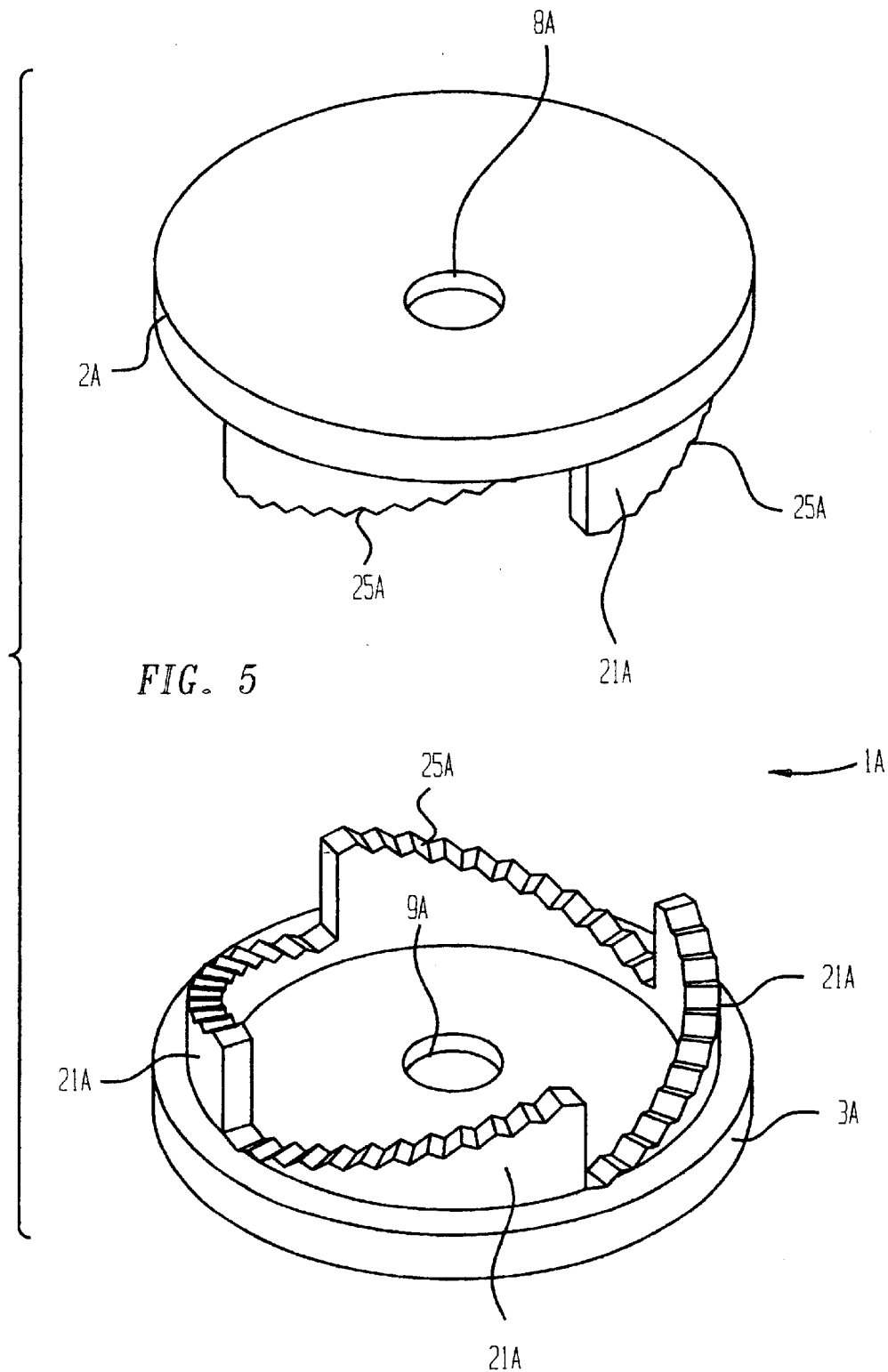
FIG. 5 is an exploded perspective view showing a modification of the prosthesis of the present invention.

Referring now to the embodiment shown FIG. 5, the two sections 2A and 3A of the cage are similar to the sections 2 and 3 of cage 1 described in the embodiment of FIGS. 1 through 4. However, in this instance, four cam surfaces 25A are shown.

Figure 6:
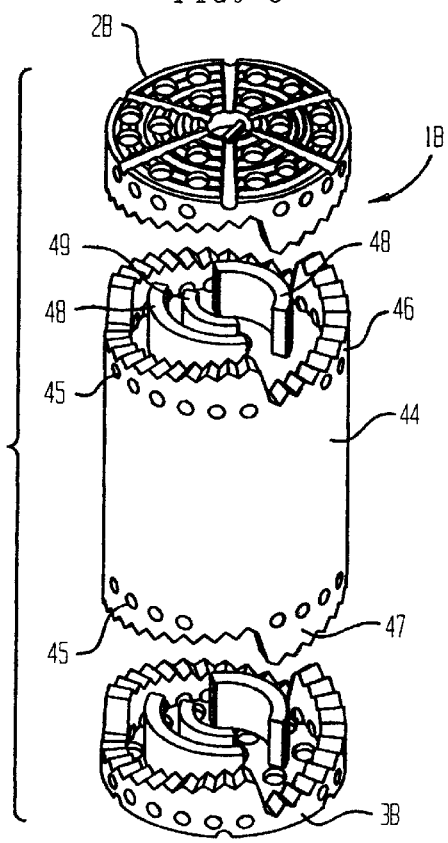
FIG. 6 is an exploded perspective view showing another modification of the present invention for vertebrae replacement.

In the embodiment shown in FIG. 6, the top and bottom sections 2B and 3B of cage 1B are similar to the sections 2 and 3 discussed above. However, an elongated connecting tube 44 is interposed between them. The top and bottom end edges of the connecting tube 44 has cam surfaces 46, teeth 47, partitions 48 and 49 and openings 45 and are similar to the cam surfaces 25, teeth 26, partitions 20 and 22 and openings 10 in the sections 2 and 3 of the FIGS. 1 through 4 embodiment. Hence, the sections 2B and 3B are complimentary to the end edges of the tube 44. With this structure, if the space between the vertebrae is very large, the connecting tube 44 is used in order to span the distance between the two sections 2B and 3B to fill the space between the vertebrae. Alternatively, the structure shown in FIG. 6 may be used to replace a vertebrae.

Figure 7:
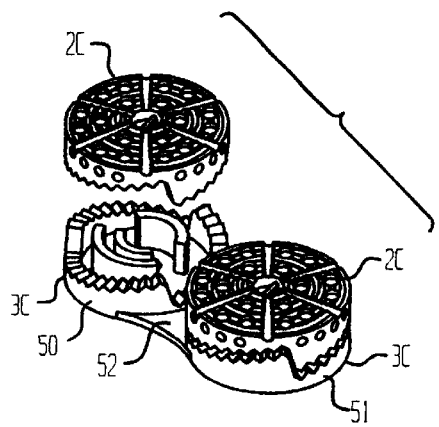
FIG. 7 shows another modification of the present invention for aligning the vertebrae.
Figure 8A:
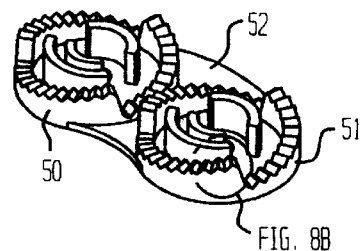
FIG. 8A is a perspective view of a part of the prosthesis shown in FIG. 7
Figure 8B:
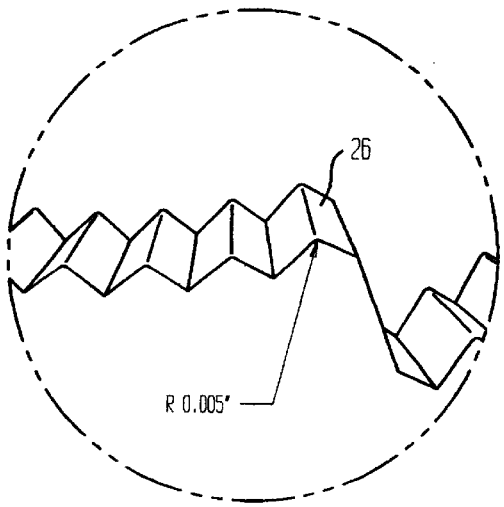
FIG. 8B is an extremely magnified detail of a portion thereof.

Referring to the embodiment shown in FIGS. 7 through 8B the prosthesis shown comprises double cages 50 and 51 which has top sections 2C similar to the top section 2 of the FIGS. 1 through 4 embodiment. The bottom sections 3C are also the same but are connected together by a web 52. The top sections 2C are rotated relative to the bottom sections 3C. The cages 50 and 51 can be adjusted to different heights depending on the spinal curvature that is desired. Adjusting the cages to different heights will cause the cages to act as a leveling device.

Figure 9:
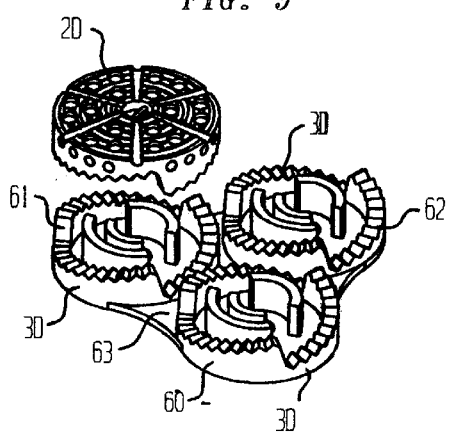
FIG. 9 is a perspective view showing another modification of the present invention for multi-directional leveling of the vertebrae.

The embodiment shown in FIG. 9 shows a prosthesis that is similar to the embodiment shown in FIGS. 7 through 8B. However, in this embodiment, three cages 60, 61 and 62 are used with the top sections 2D of each (only one is shown) being the same as the top section 2 of the FIGS. 1 through 4 embodiment and the bottom sections 3D being connected together by a web 63. Again, the cages 60, 61 and 62 can be individually adjusted to different heights to act as a leveling device that allows multi-directional flexibility without sacrificing stability and restores natural mobility of the vertebrae.

Figure 10A:
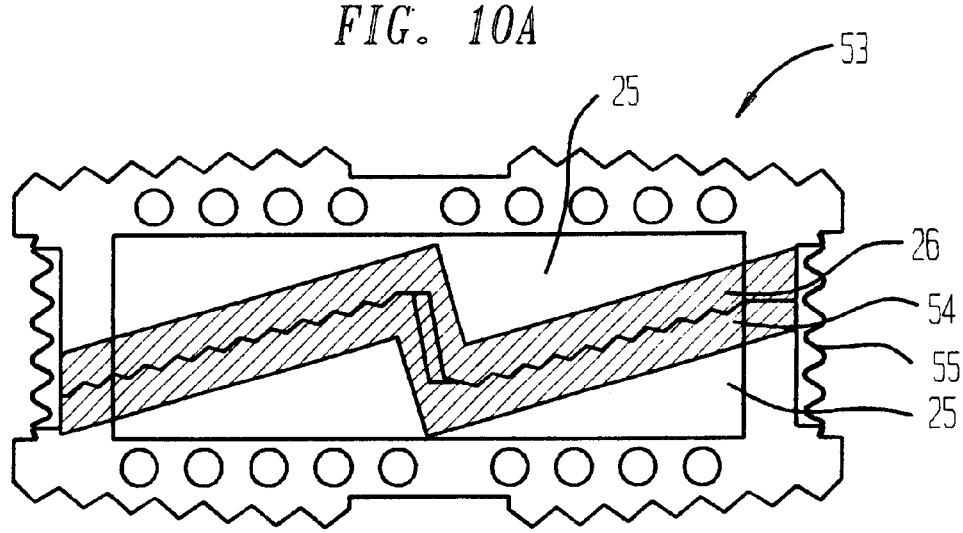
FIGS. 10A through 10C are several views of another embodiment of the present invention as a flexible prosthesis partially made of a bio-resorbable material.
Figure 10B:
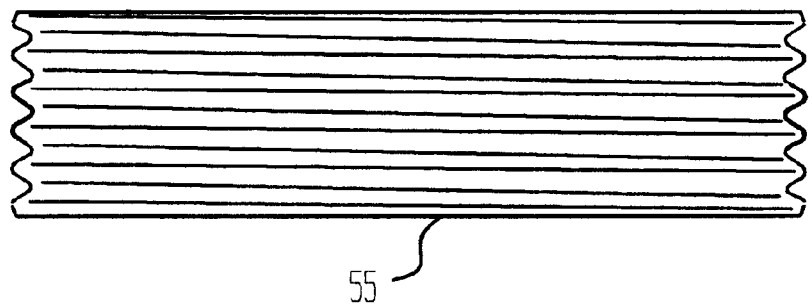
Figure 10C:
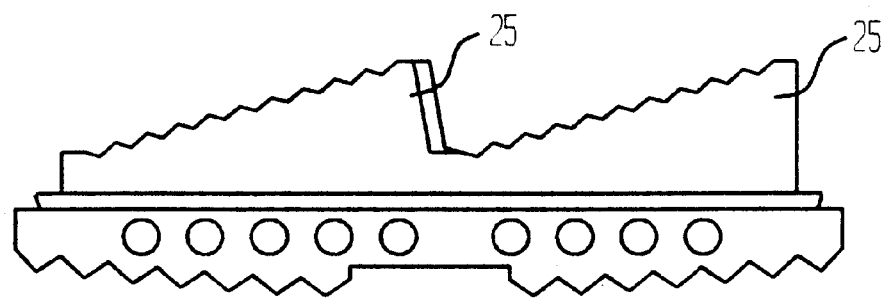

FIGS. 10A through 10C show another embodiment of the present invention. A cage 53 is similar to the cage described in connection to FIG. 1. However, the outer edge 54 of the cam surfaces 25 and the teeth 26 are made of a bio-resorbable material. A titanium bellows 55 surrounds the cage 53. The bio-resorbable material between the upper and lower sections of cage 53 will degrade eventually and leaving the bellows 55 to give the cage multi-directional flexibility without causing associated instability.

Figure 11A:
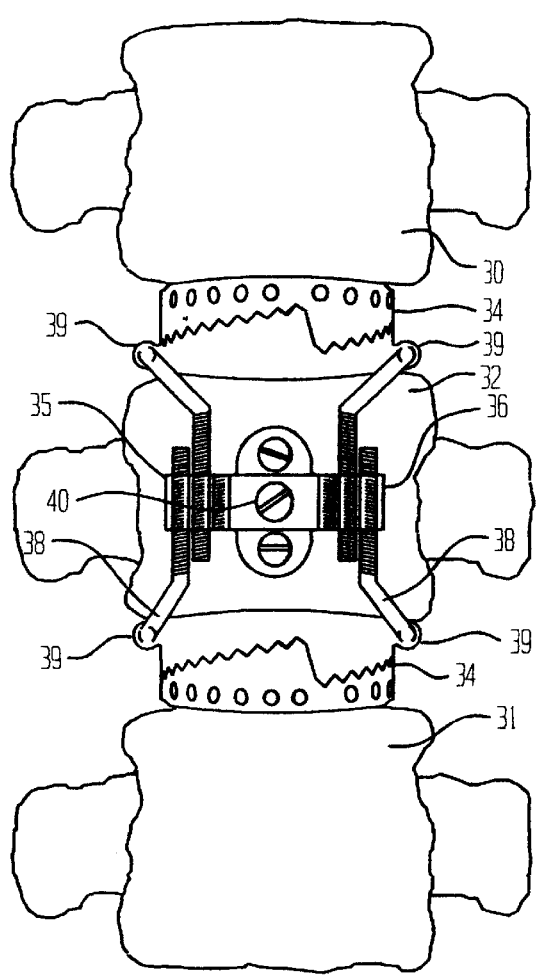
FIGS. 11A through 11D are several views of another embodiment of the present invention for two level stabilization of the vertebrae.
Figure 11B:
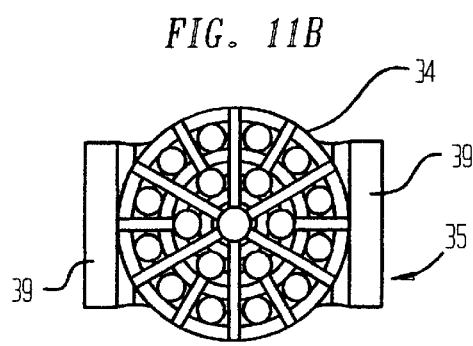
Figure 11C:
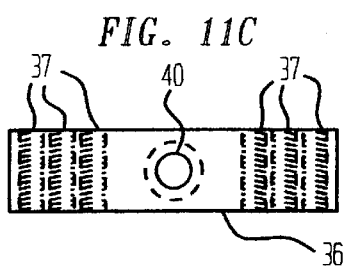
Figure 11D:
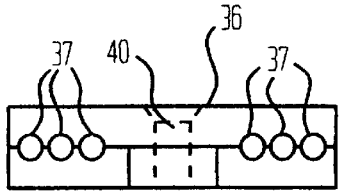
Figure 12A:
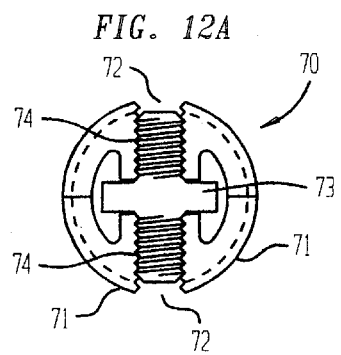
FIGS. 12A through 12I are several views of another modification of the present invention.
Figure 12D:
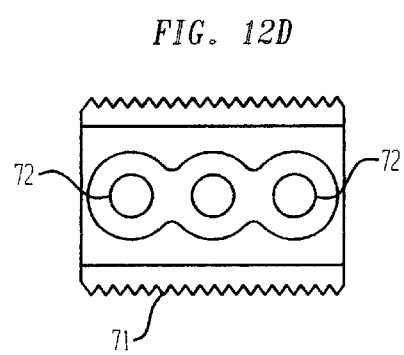
Figure 12G:
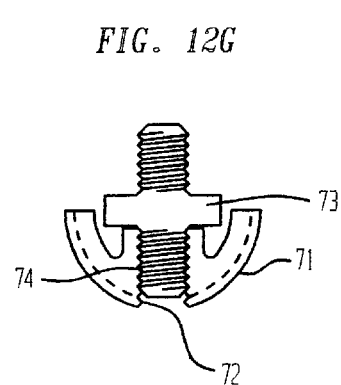
Figure 12B:
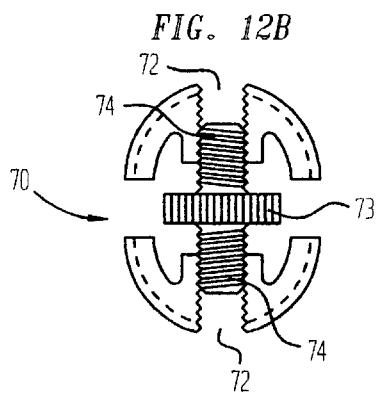
Figure 12E:
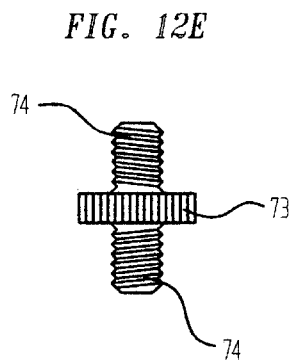
Figure 12H:
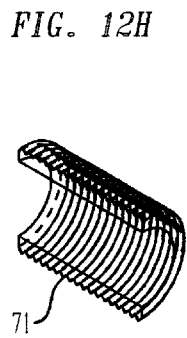
Figure 12C:
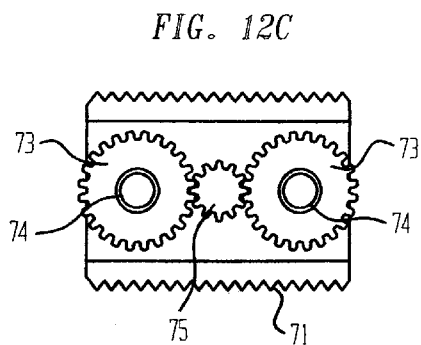
Figure 12F:
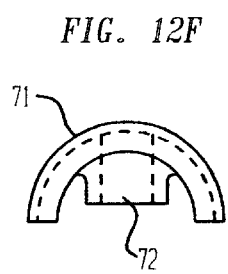
Figure 12I:
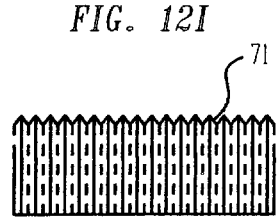
Figure 13A:
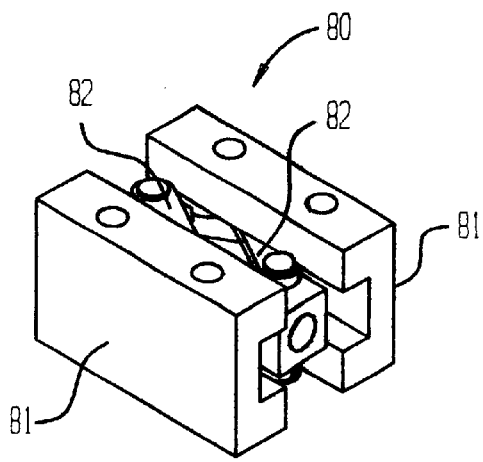
FIGS. 13A through 13D are several views of another modification of the present invention.
Figure 13B:
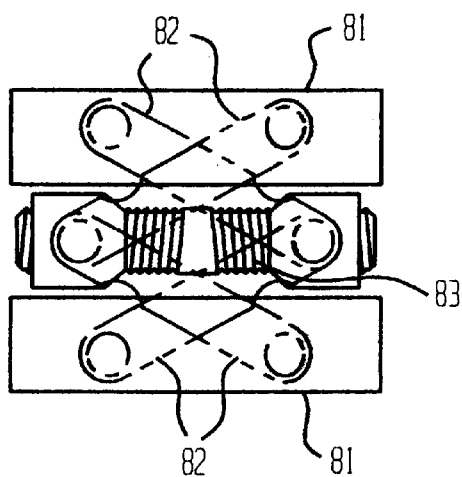
Figure 13C:
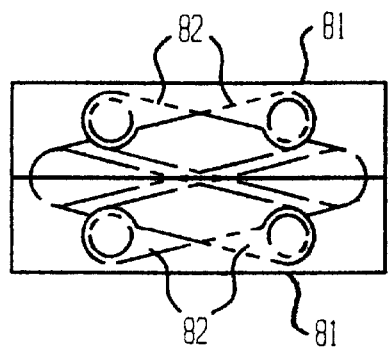
Figure 13D:
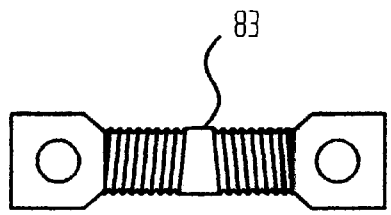

FIGS. 11A through 11D show another embodiment of the present invention. In this embodiment, an upper vertebrae, 30, a lower vertebrae 31, and an intermediate vertebrae 32, are to be linked together. A cage 34 similar to the cage described in connection with FIG. 1, is inserted between the upper vertebrae 30 and the intermediate vertebrae 32, and another similar cage 34 is inserted between the lower vertebrae 31 and the intermediate vertebrae 30. A connecting and stabilizing assembly 35 is provided to connect the two cages 34 and to connect and stabilize all the vertebrae 30, 31 and 32. The connecting assembly 35 comprises a clamping plate 36 having a plurality of threaded openings 37 therein. The clamping plate 36 is to be screwed or otherwise mounted to the central vertebrae 32 by a screw or some other suitable means 40. Connecting rods 38 are threadably inserted through the openings 37 in the clamping plate 36. The outer ends of the connecting rods 38 have holding knobs 39 which bear against the outer surfaces of each cage 34 on each side thereof as shown in FIG. 11B. With this structure the clamping plate 31 is affixed to the intermediate vertebrae 32 and the holding knobs 39 of each connecting rod 38 extends along both sides of each of the cages 34 and stabilizes the cages and the vertebrae 30, 31 and 32.

Referring now to the embodiment in FIGS. 12A to 12I, a gear type expansion cage 70 is shown. The expansion cage 70 comprises a pair of curved elongated outer bearing surfaces 71 each of which have a geared threaded opening 72 therein. A gear wheel 73 has threaded extensions 74 on each side thereof which are inserted in the threaded openings 72 in each of the curved bearing surfaces 71. A pair of such gears 73 with threaded extensions 74 is mounted on each end of the bearing surfaces 71 and the two gears 73 are connected together by a central gear 75. When one of the gears 73 is rotated, that end of the bearing surface 71 will expand or contract depending on the direction that the gear 73 is turned and at the same time, the central gear wheel 75 will also rotate the second gear 73 in order to expand that side of the curved bearing surface 71. In this manner, the curved bearing surfaces 71 will move away or toward each other to fill the gap between the vertebrae. The outer surfaces of the bearing surfaces 71 have grooves 76 to permit and enhance fusing the prosthesis with bone.

Referring now to the embodiment shown in FIGS. 13A through 13D, a jack-type cage 80 is shown. A pair of opposed bearing surfaces 81 (shown elongated and flat—but which may be curved) are connected together by a plurality of cross arms 82 through the intermediation of a jack screw 83. The ends of the arms 82 are connected to each end of the two bearing surfaces 81 and to each end of the jack screw 83. Rotating the jack-screw 83 in one direction or the other extends or contracts the arms 82 in either one direction or the other to either move the bearing surfaces 81 away from each other or to move them toward each other. In this manner, the bearing surfaces 81 will fill the gap between vertebrae.

Figure 14A:
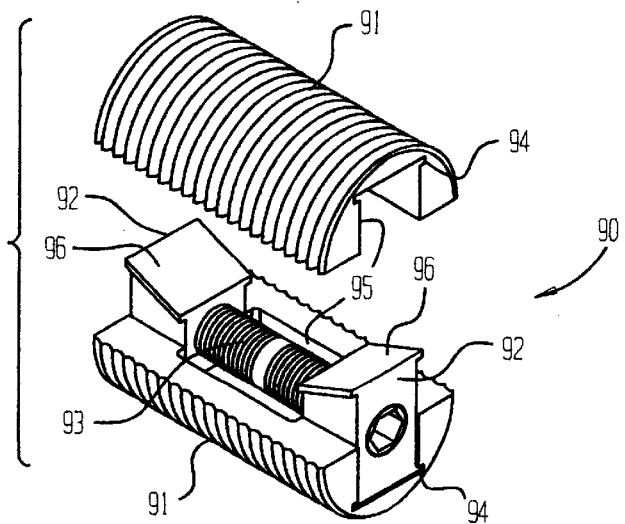
FIGS. 14A through 14C are several views showing another modification of the present invention.
Figure 14B:
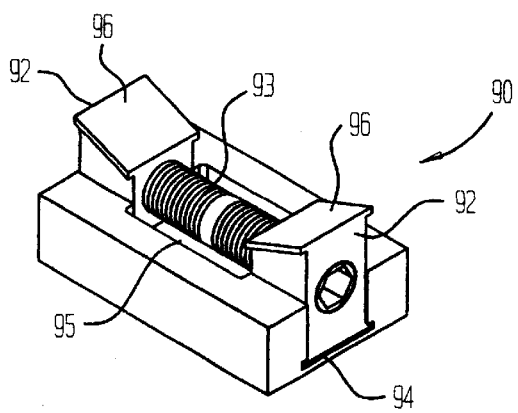
Figure 14C:
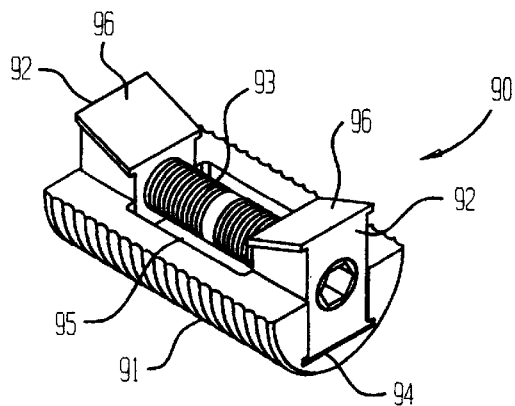

In the embodiment shown in FIGS. 14A through 14C, a wedge type cage 90 is described. The curved elongated outer bearing surfaces 91 have a pair of wedges 92 therebetween which are controlled and connected together by a screw 93. The wedges 92 are adapted to move in grooves 94 in the inner channels 95 in the bearing surfaces 91. The wedges 92 having opposed inclined surfaces 96. By rotating the screw 93 in one direction or the other the wedges 92 are moved closer or further apart from each other and since the surfaces 96 are angled in opposite directions, the two bearing surfaces 91 are moved towards or away from each other. In this manner, the space between the vertebrae may be filled by merely adjusting the height of the two bearing surfaces 91, as described above.

Figure 15A:
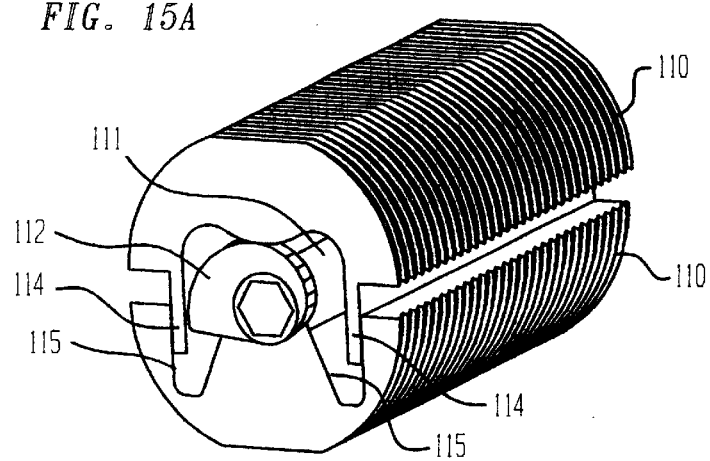
FIGS. 15A through 15C are several views showing another modification of the present invention.
Figure 15B:
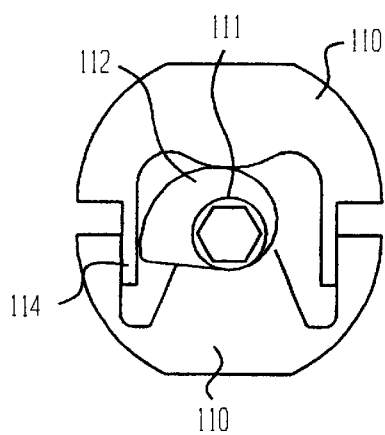
Figure 15C:
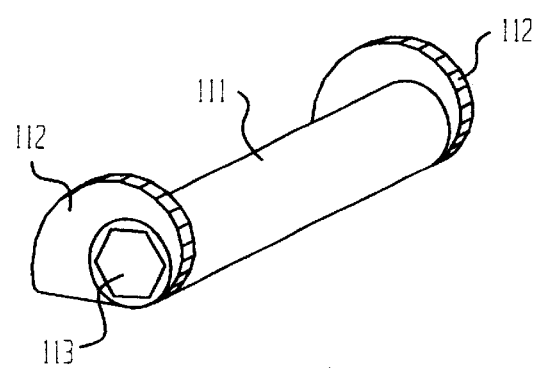

FIGS. 15A through 15C show a cam type expandable cage. In this embodiment, the opposed curved elongated bearing surfaces 110 have a rod 111 interposed between them with cams 112 in each end. The rod 111 has an opening 113 at its edges which permit the rod 111 and the cams 112 to be rotated. When the rod 111 is rotated, the cams 112 will rotate and strike the interior of the two bearing surfaces 110 to move the two bearing surfaces 110 towards or away from each other. A pair of elongated guides 114 extend from the interior of one of the bearing surfaces 110, which correspond to a pair of grooves 115 on the interior of the opposite bearing surface 110, to prevent lateral movement and dislodgment of the opposed bearing surfaces 110 from each other.

Figure 16:
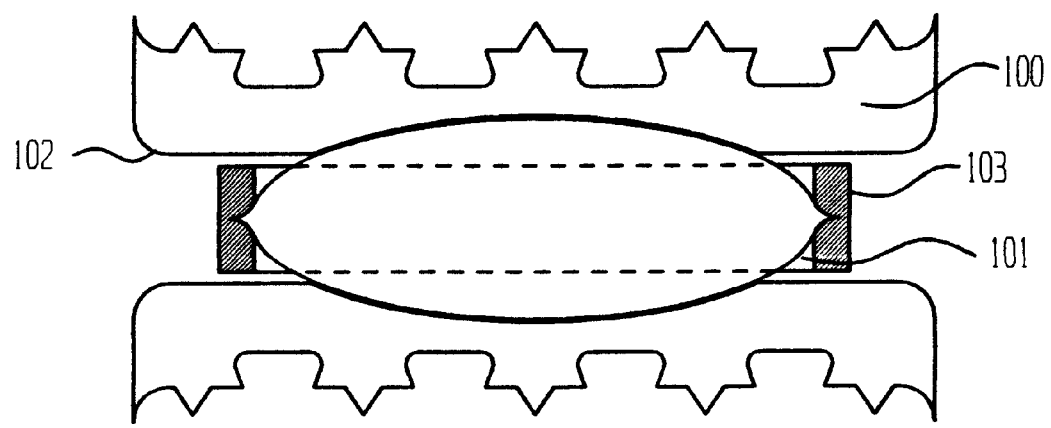
FIG. 16 show another modification of the present invention.

Referring to the embodiment of FIG. 16, a flexible spinal fusion prosthesis is shown in which upper and lower plate members 100 and 101 are provided with an intermediate convex flexible disc 102 interposed therebetween. The disk 102 may be made of titanium or some other known material which is biocompatible and compressible. A rigid collar 103 of resorbable material surrounds the disc 102 to make the flexible disc 102 rigid in order to allow integration of the upper and lower plate members 100 and 101 with the bones of the vertebrae. The collar 103 will be resorbed and thereafter the flexible disc 102 will function in a flexible manner between the vertebrae.

Figure 2:
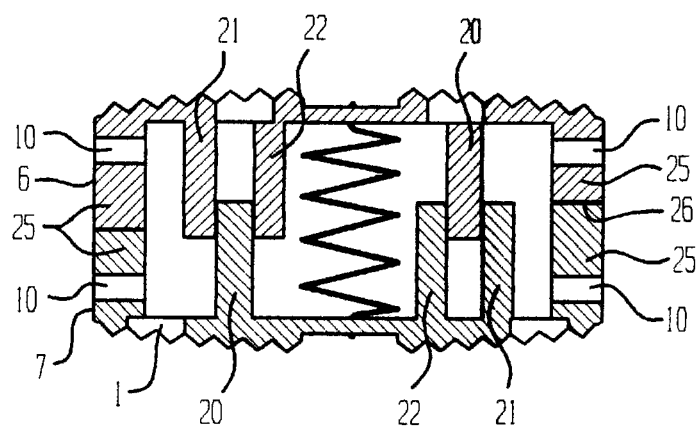
FIG. 2 is a cross-sectional view of the prosthesis, with a spring biasing the top and bottom sections.
Figure 17A:
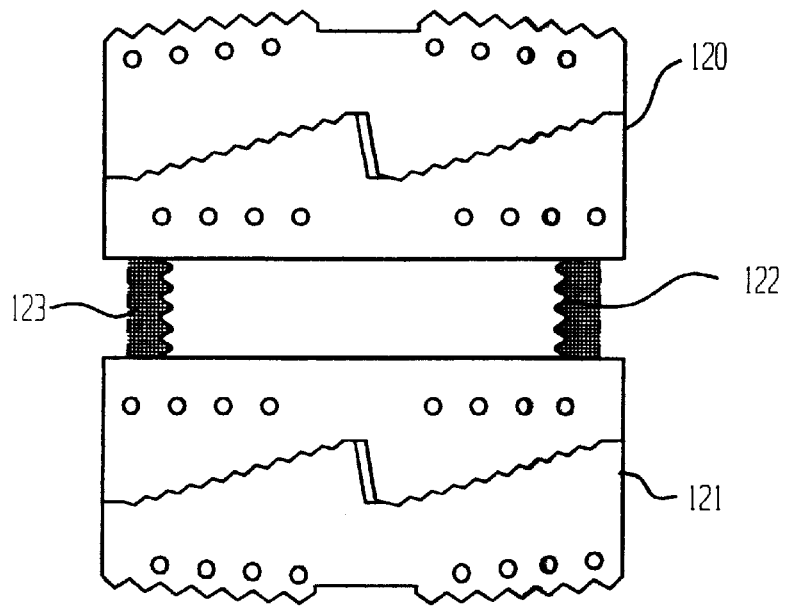
FIGS. 17A through 17C are several views showing another modification of the present invention.
Figure 17B:
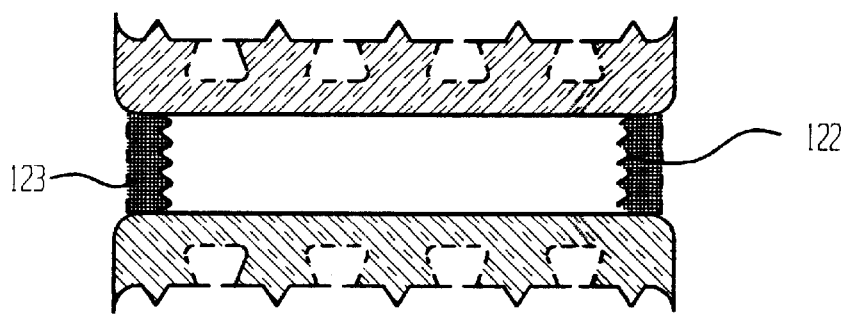
Figure 17C:
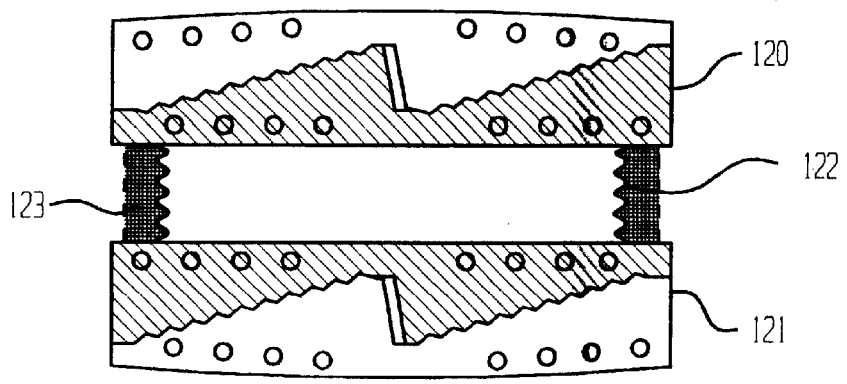
Figure 18A:
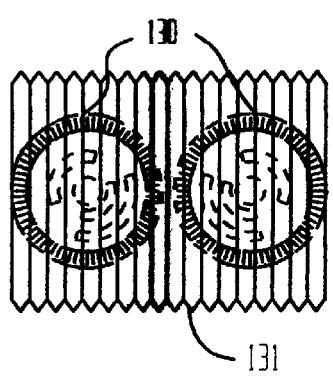
FIGS. 18A through 18G are several views showing another modification of the present invention.
Figure 18B:
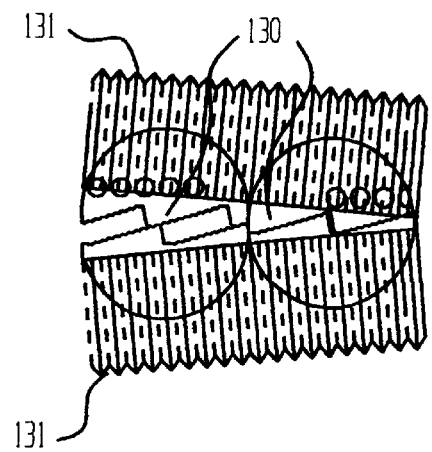
Figure 18C:
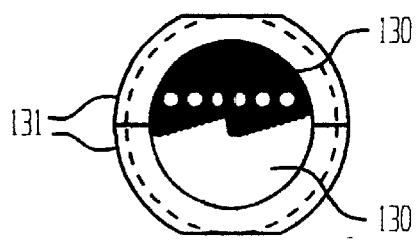
Figure 18D:
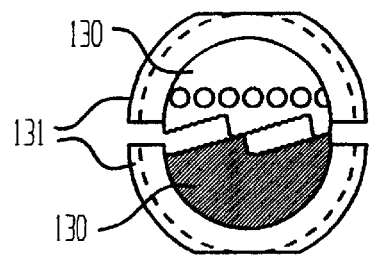
Figure 18E:
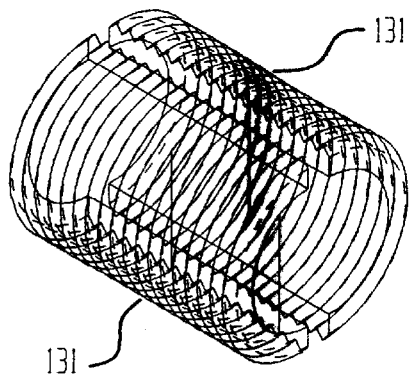
Figure 18F:
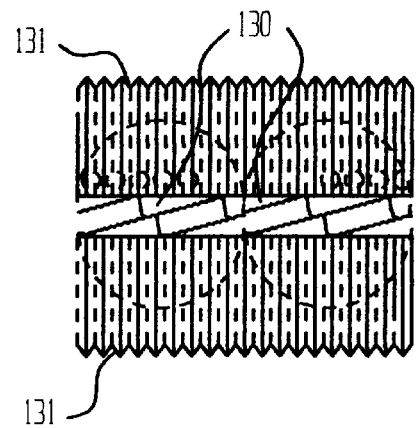
Figure 18G:
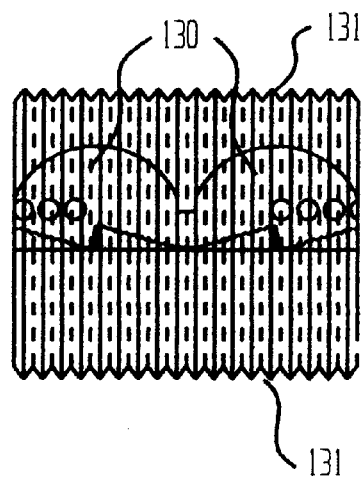

With respect to the embodiment shown in FIGS. 17A to 17C, a pair of expandable cages 120 and 121 similar to the cages of FIGS. 1 and 2 are mounted between vertebrae in a spaced relationship to each other. A titanium bellows-like assembly 122 is interposed between the spaced cages 120 and 121. Resorbable rigid material 123 surrounds the bellows 122 and make the bellows 122 rigid until the resorbable rigid material 123 is absorbed, after which the bellows 122 will become flexible to act as a cushion between the two cages 120 and 121. If desired the space between the bellows 122 may be filled with a polymer.

In the embodiment shown in FIGS. 18A to 18G, a plurality of expandable cages 130 similar to the cage 1 of FIGS. 1 through 4, are interposed between a pair of curved elongated bearing surfaces 131 so that contact with the vertebrae is made by the curved bearing surfaces 131 rather than by the expansion cages 130 themselves. The internal expansion cages 130 can be adjusted to different heights to permit the bearing surfaces 131 to achieve different heights and angles.

Figure 19:
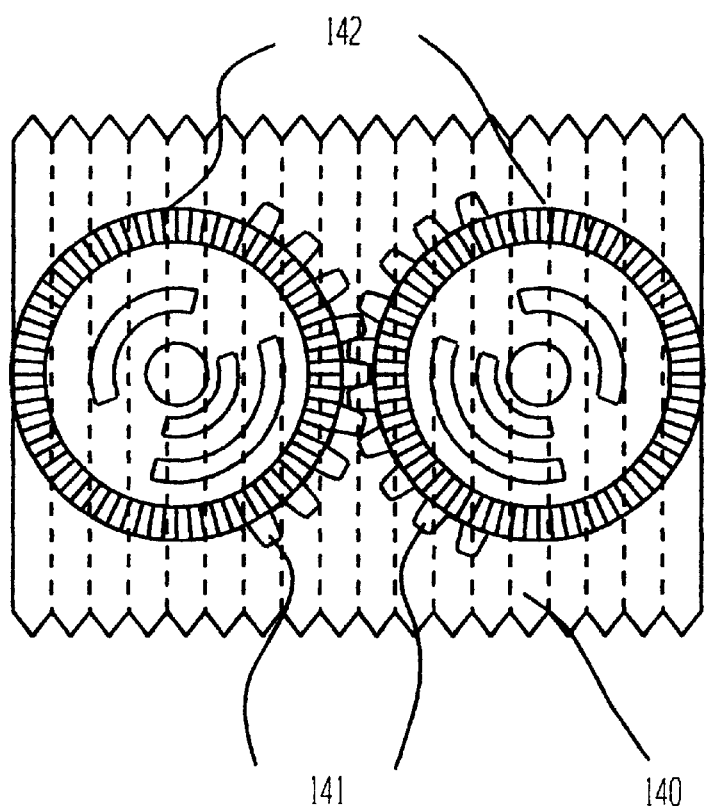
FIG. 19 shows still another modification of the present invention.
Figure 20A:
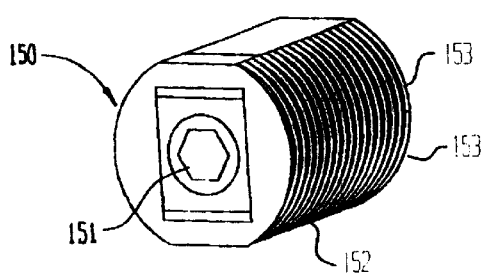
FIGS. 20A through 20F are several views showing still another modification of the present invention.
Figure 20B:
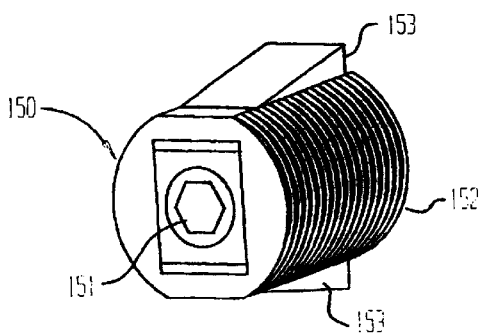
Figure 20C:
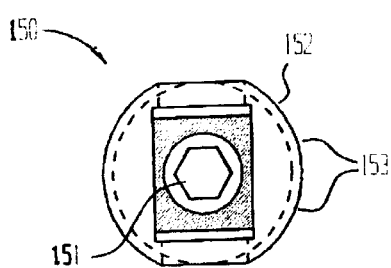
Figure 20D:
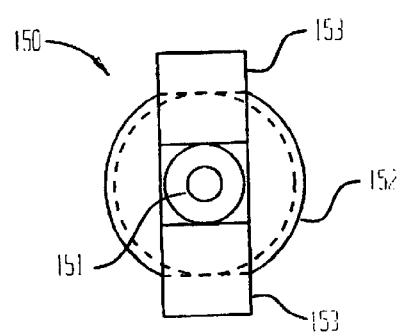
Figure 20E:
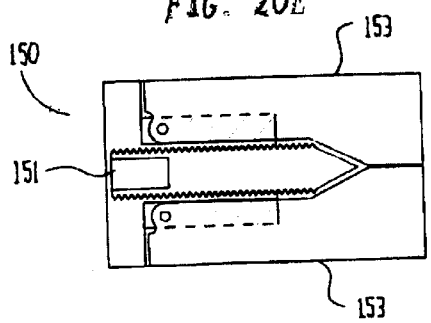
Figure 20F:
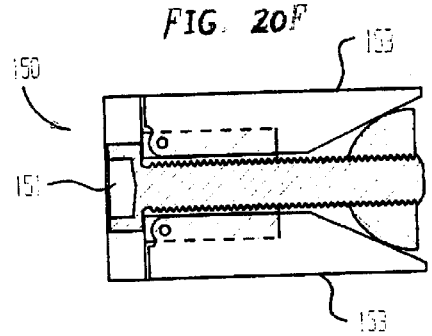
Figure 3:
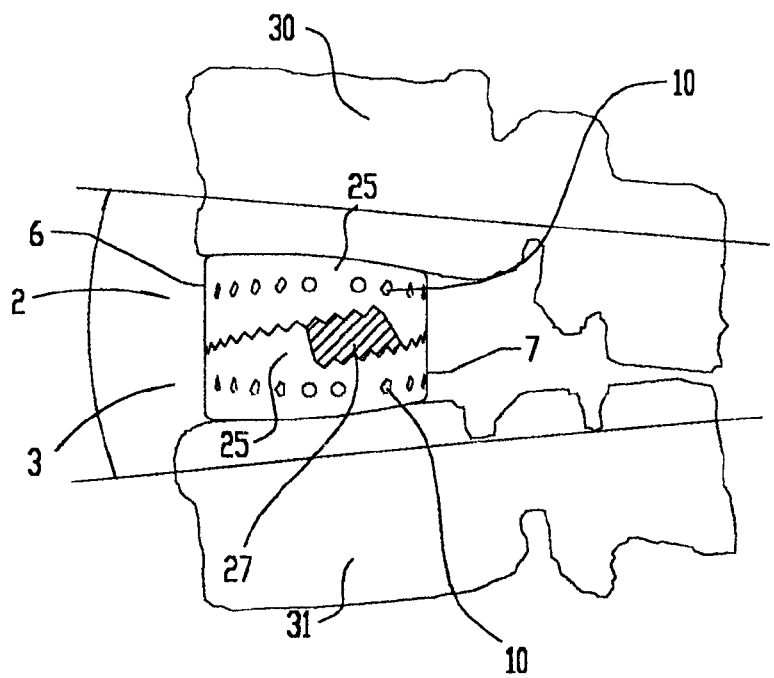
Figure 4:
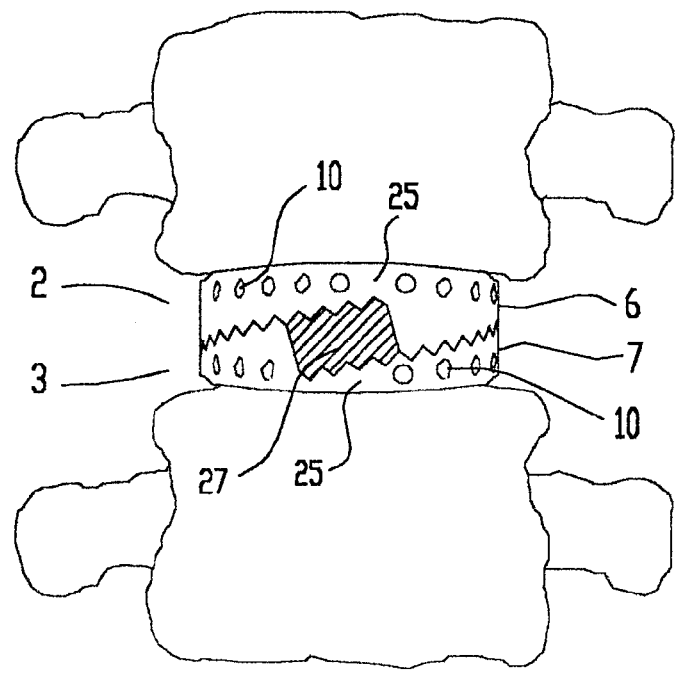
Figure 16:
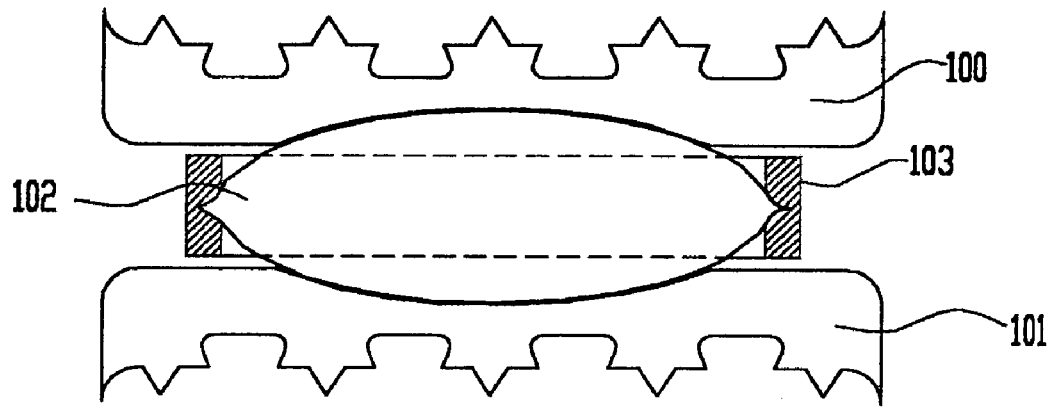

In the embodiment shown in FIG. 19 the elongated curved bearing surfaces 140 have a pair of cages 142 similar to the cage shown in FIG. 1. Each cage has an outer gear 141 extending from its outer surface. When the gears 141 are rotated in one direction, the bearing surfaces 140 are moved towards each other.

It will be noted that in FIG. 19 the two gears are the same size and ratio. However, it is within the purview of the present invention for the two gears to be of different ratios and sizes so that movement of one gear will expand its cage to a certain height, and the other cage, having a gear of a different ratio, will expand its cage to a different height. This may also be accomplished by a connecting gear between the two gears (not shown). It is also possible to accomplish the same purpose by having geared teeth of different heights so that the two geared cages may move to different expansions.

Referring to the embodiment shown in FIGS. 20A through 20F, a tapered expandable cage 150 is shown. An expansion screw 151 is mounted in the cage 150 having a circular solid front portion 152 and expandable curved rear bearing surfaces 153. By rotating the screw 151, the inner edge of the screw 151 will contact the expandable bearing surfaces 153 and expand them. In version A (FIG. 20E), the expandable screw 151 has a point 154 which moves toward the expandable bearing surfaces 153 and spreads them apart. In version B (FIG. 20F), the expansion screw 151 has a tapered blunt edge 155 which contacts the expandable bearing surfaces 153 and spreads them apart.

It will thus be seen that the present invention provides improved means for achieving fusion of the inter-vertebral space and stabilization as a single procedure in a manner consistent with the conventional methods of disectomy and re-establishing the ideal and normal pre-existing disc interspace which is easier, quicker, safer, and entails less blood loss than other known means. The present invention also achieves one stage inter-space fusion and stabilization with minimal damage and less removal of bone from the surface of the adjacent vertebrae and establishes the normal and pre-existing inter-vertebral space in an easy, quick, safe and precise manner. In addition, the present invention provides a method and device of inter-vertebral arthrodesis and stabilization that allows for the inter-vertebral space to be adjustable and of variable sizes and with greater simplicity and accuracy than any other known means by the use of a modular prosthesis having similar and multiple attachments that allows for insertion through a small incision and to reconstitute the inter-space occupying device into a much larger spacing member so as to fit the contours of any inter-space without the need to sacrifice any vertebral bone. The prosthesis of the present invention provides for an implant that has means for osseous integration with the adjacent vertebrae which can also act as a shock absorber when extremely heavy forces are exerted upon it and which permits the reestablishment of normal lordosis of the spine in a simple and precise manner and provides a method and biocompatible material for inducing bone growth that can readily be shaped into a desired form.

The present invention also provides a biocompatible material and method for controlling hemostasis thereby enhancing osseous integration in individuals with abnormal clotting problems and may also act over a prolonged period of time to control post-operative bleeding. With this invention, post-operative pain and infection are controlled and application of anti-tumor drugs or radiation beads may be easily administered by being time released locally and/or in combination with systemic drugs for this purpose.

As many varied modifications of the subject matter of this invention will become apparent to those skilled in the art from the detailed description given hereinabove, it will be understood that the present invention is limited only as provided in the claims appended hereto.

The embodiments of the invention in which an exclusive property or privilege is claimed are defined as follows:

1. A prosthesis comprising:
   (a) at least one set of opposed complimentary bearing surface assemblies, each of said bearing surface assemblies comprises top and bottom sections, each section having an outer bearing surface with an inner face and a wall extending therefrom, said wall comprising a plurality of inclined cam surface extending substantially vertically from the inner face of said bearing surface and away therefrom;
   (b) means for moving said bearing surface assemblies towards and away from each other, said moving means being integral of the bearing surface assemblies, whereby movement by the moving means in one direction will move the bearing surface assemblies away from each other and movement by moving means in the opposition direction will move the bearing surface assemblies towards each other, thereby increasing and decreasing, respectively, the height of said prosthesis; and
   (c) partition means extending substantially vertically and away from the inner face of said bearing surface of each section comprises a pair of outer partitions and an inner partition, wherein said outer partitions of said top section engage said inner partition of said bottom section and said outer partitions of said bottom section engage said inner partition of said top section to allow movement of said top section relative to said bottom section.

2. The prosthesis as set forth in claim 1 wherein each of said cam surfaces having an edge, teeth are provided at said edge of said cam surfaces.

3. The prosthesis as set forth in claim 2 wherein openings are provided in each of said wall to facilitate movement of said top section relative to said bottom section.

4. The prosthesis as set forth in claim 2 wherein an opening is provided in the center of each of said outer bearing surfaces.

5. The prosthesis as set forth in claim 2 wherein ridges are provided on the outer bearing surfaces of each of said bearing surface assemblies.

6. The prosthesis as set forth in claim 2 wherein channels are provided on the outer bearing surfaces of each of said bearing surface assemblies, said channels radiating outwardly from the center of said outer bearing surfaces.

7. The prosthesis as set forth in claim 2 wherein means are mounted between said top and bottom sections in order to bias said top and bottom sections toward each other.

8. The prosthesis as set forth in claim 7 in which said biasing means are spring means.

9. The prosthesis as set forth in claim 2 in which all the outer bearing surfaces of said bearing surface assemblies are supported.

10. The prosthesis as set forth in claim 9 which said teeth of said top section corresponds with said teeth of said bottom section such that said teeth from said top and bottom sections are contained within said prosthesis.

11. The prosthesis as set forth in claim 2 which said wall and said cam surfaces are curved.

12. The prosthesis as set forth in claim 2 in which said teeth having rounded edges.

13. The prosthesis as set forth in claim 2 in which a plurality of openings are provided on said outer bearing surfaces.

14. The prosthesis as set forth in claim 2 further comprises a substantially rigid bio-resorbable material between said edges of said cam surfaces and a bellows adjacent to said bearing surface assemblies.

15. The prosthesis as set forth in claim 14 further comprises an elastomeric polymer between said bellows.

16. The prosthesis as set forth in claim 2 further comprises means interposed between said two sections for connecting said two sections, said connecting means having opposite ends, each end of said connecting means having inclined cam surfaces, teeth on its edges, and inner and outer partitions thereof whereby said connecting means may be moved relative to the two sections to increase or decrease the height of the prosthesis.

17. The prosthesis as set forth in claim 2 comprising two or more sets of opposed complimentary bearing surface assemblies, wherein said bottom sections of said two or more sets are joined together by a web and each of said set of bearing surface assemblies being individually and independently adjustable to act as a leveling device.

18. The prosthesis as set forth in claim 1 further comprises a substantially rigid bio-resorbable material adjacent to said bearing surface assemblies and a flexible resilient bearing means mounted adjacent and engaging said bearing surface assemblies, whereby upon degradation of said bio-resorbable material, said flexible resilient means remains adjacent said bearing surface assemblies.

* * * * *

UNITED STATES PATENT AND TRADEMARK OFFICE
CERTIFICATE OF CORRECTION

PATENT NO.    : 6,454,806 B1
DATED         : September 24, 2002
INVENTOR(S)   : Howard Cohen, Ladislau and Matthew S. Cohen It is certified that error appears in the above-identified patent and that said Letters Patent is hereby corrected as shown below:

Replace Figures 3, 4 and 16 with the enclosed Figures 3, 4 and 16.

Signed and Sealed this

Sixth Day of April, 2004

JON W. DUDAS
*Acting Director of the United States Patent and Trademark Office*